United States Patent [19]

Schroeder et al.

[11] Patent Number: 4,743,577

[45] Date of Patent: May 10, 1988

[54] CATALYST COMPOSITION

[75] Inventors: Hobe Schroeder, Warrenville; Ricky L. Wittman, Montgomery, both of Ill.

[73] Assignee: Amoco Corporation, Chicago, Ill.

[21] Appl. No.: 918,390

[22] Filed: Oct. 14, 1986

[51] Int. Cl.$^4$ .................... B01J 21/06; B01J 23/72; B01J 23/89
[52] U.S. Cl. .................... 502/326; 502/331; 502/339
[58] Field of Search ............... 502/313, 314, 326, 331, 502/339

[56] References Cited

U.S. PATENT DOCUMENTS

| | | | |
|---|---|---|---|
| 3,773,894 | 11/1973 | Bernstein et al. | 502/314 X |
| 3,867,313 | 2/1975 | Brewer | 502/314 |
| 4,252,690 | 2/1981 | Kamiya et al. | 502/300 X |
| 4,410,454 | 10/1983 | Faschingbauer | 502/326 X |

*Primary Examiner*—W. J. Shine
*Attorney, Agent, or Firm*—James R. Henes; William H. Magidson; Ralph C. Medhurst

[57] ABSTRACT

Metallic catalysts are improved in performance and life when extended as a thin surface layer upon a porous, sintered metal substrate, particularly when employed in hydrogenation or decarbonylation reactions.

17 Claims, No Drawings

CATALYST COMPOSITION

BACKGROUND OF THE INVENTION

In the purification of oxidation products, as, for example, terephthalic acid derived from the oxidation of p-xylene, major impurities include partially oxidized compounds, such as 4-carboxybenzaldehyde. This impurity can be substantially removed by hydrogenation of the aldehyde functional group to a methylol group or by decarbonylation with removal of the carbon-containing substituent group. Such modification of the impurity components converts them to products which can be more readily removed from the desired terephthalic acid product than can the original impurity components from which they were formed.

In purification steps, as outlined above, a customary catalyst consists of palladium metal finely dispersed upon granules of activated coconut shell charcoal. Although such catalysts possess generally acceptable physical properties, the carbon granulates abrade easily, thus causing a new and different type of product contamination as well as leading to poor recovery of the palladium component.

Both palladium recovery and catalyst fines contamination are related to catalyst physical properties such as crush strength, abrasion resistance and fines content. There remains a need, and it is an object of this invention to provide, a catalyst composition with a better catalyst support having improved physical properties. Other objects and advantages of the present invention will become apparent upon reading the following detailed description and appended claims.

It has now been found that high-activity metal catalysts, having improved physical properties, may be obtained by the use of metallic support, particularly by the use of a porous, sintered metal as the catalyst substrate. Sintered metals are readily available so that such catalysts become practical and economically attractive.

In the past, metal catalysts have been modified in various ways to achieve improved performance or improved physical characteristics. For example, U.S. Pat. No. 3,123,574 discloses the treatment of a palladium/charcoal catalyst with a salt of silver, mercury, or bismuth to improve hydrogenation of fatty oils. In U.S. Pat. No. 3,928,237, catalysts for suppressing emissions from internal combustion engines are prepared by first absorbing a metal-ammonia complex on a selected substrate, preferably alumina, and then decomposing the complex to afford the free metal. Separate preparations of different metals may be combined in use. In U.S. Pat. No. 4,187,200, an alloy of two metals is created on a support surface, one of the metals being converted to a volatile compound and removed to leave an active catalytic metal in porous form on a support which may be metallic or non-metallic.

SUMMARY OF THE INVENTION

This invention relates to a catalyst composition comprising a first active, catalytic metal disposed or extended as a thin metallic layer upon the surface of a second metal present in the form of a porous, sintered substrate, wherein the first metal is present at a level of 0.1-10 weight percent calculated as the elemental first metal and based on the weight of the catalyst composition. Such catalytic metals may be selected from those active for hydrogenation, deoxygenation, decarbonylation, or other suitable chemical conversions. Such support metals include those having relatively high melting points but whose powders can be readily sintered to afford a porous matrix.

The catalytic metals of this invention include palladium, nickel and rhodium, as well as platinum, copper, ruthenium, cobalt and suitable mixtures of any of these metals.

The support metals of this invention include titanium, zirconium, tungsten, chromium, nickel and alloys incorporating one or more of these metals. Preferred support metals include titanium, nickel and the alloy Inconel, whose principal components are nickel, chromium and iron and the alloy stainless steel.

This invention further relates to catalyst compositions wherein an intermediate metal layer is first disposed or extended upon the surface of the support metal. If present, the intermediate metal is present at a level of 0.1-10 weight percent, calculated as the elemental intermediate metal and based on the weight of the catalyst composition. Preferred intermediate metals include copper, nickel, platinum and mixtures of these metals.

More particular embodiments of the monolithic metal catalysts of this invention relate to catalysts having a high and improved activity for use in process steps such as hydrogenation and decarbonylation. Particularly desirable catalysts are those suitable for use in the purification of terephthalic acid, especially for the removal of contaminants such as 4-carboxybenzaldehyde.

DESCRIPTION OF THE INVENTION

The catalyst compositions of this invention generally comprise a porous, sintered metal support component together with a catalytic metal component extended upon the surface of the support component. In some instances a third metal layer is afforded intermediate the catalytic and support components. The catalyst compositions exhibit improved properties when employed in various catalytic conversions such as hydrogenation, decarbonylation and the like.

Porous, sintered metal support components may, for example, be prepared by heating the powdered metal substantially in accordance with the disclosure of U.S. Pat. No. 2,997,777, which is incorporated herein by reference in its entirety. The metal powder, having a particle size generally within the range from −100 to +325 mesh, is heated under conditions of time, temperature and pressure to provide a sintered mass having a pore diameter within the range from about 1 to about 10 microns and a surface area within the range from about 0.01 to about 2.0 square meters per gram. Although other metals, such as zirconium tungsten, and chromium, may be employed, the preferred support metals are titanium, nickel and alloys comprising one or more of the support metals. Preferred alloys are stainless steel and nickel-chromium-iron alloy, known in the trade as Inconel.

Catalytic metals may be dispersed upon the support metal surface in relatively thin layers employing any effective method, although a preferred technique comprises electroplating from solution of a salt of the selected outer surface metal under controlled conditions to achieve the desired concentration of catalytic metal with a substantially uniform distribution thereof on the surface of the sintered support metal. The catalyst metal may be selected from among palladium, nickel, rhodium, platinum, copper, ruthenium, cobalt and mixtures of any of these. Preferred catalytic metals are palladium, nickel and rhodium. The concentration of the first catalytic metal in the catalyst composition of this invention is in the range of from about 0.1 to about 10 weight percent, calculated as the elemental first metal and based on the weight of the final catalyst composition.

Whenever an intermediate metal layer is employed, it is preferably extended upon the surface of the support metal matrix by electroplating from a solution of a salt of the selected intermediate metal. Suitable intermediate layer metals include copper, nickel, platinum and mixtures of these metals. The concentration of the intermediate metal in the catalyst composition of this invention is in the range of from about 0.1 to about 10 weight percent, calculated as the elemental intermediate metal and based on the weight of the final catalyst composition.

When such metal catalysts, afforded on a porous, sintered metallic surface, are employed in the preparation of purified terephthalic acid by the hydrogenation of an aqueous solution of crude terephthalic acid at elevated temperature, the major impurity, 4-carboxybenzaldehyde is converted either to 4-hydroxymethyl benzoic acid, 4-toluic acid, or benzoic acid. All of these products can be removed from purified terephthalic acid more readily than can 4-carboxybenzaldehyde. The surprising effectiveness of such monolithic metal catalysts, when compared with conventional metal/carbon or metal/alumina catalysts, wherein the substrate possesses a very high surface area, is believed to be due to the nature of the porous structure of the sintered support metal.

The surface area of a porous metal is extremely small. When compared to that of a conventional support material, such as activated carbon, whose surface area is usually about 1,000 square meters per gram, the surface area of the porous support metal is less by a factor exceeding four orders of magnitude. Surprisingly, a significant increase in surface area occurs upon the plating of the support metal with one of the catalytic metals. For example, a four-fold increase in surface area is observed after plating a porous, sintered titanium support with palladium. Even greater increases are observed when employing porous nickel or porous Inconel, as shown in Table I. (In Table I, the palladium concentration is reported as weight percent of elemental palladium of the weight of the catalyst composition.) A palladium surface area of 0.2 m$^2$/g of catalyst is approximately that of a commercial catalyst for the purification of crude terephthalic acid after aging at 530° F. Because of the greater density of porous metal catalysts, when compared with conventional catalysts for the purification of crude terephthalic acid, the surface area comparison becomes more favorable for the all-metal catalysts when made on an equal volume basis. The bulk density of porous, sintered titanium is 3.3 g/cm$^3$ where that of conventional catalyst on a carbon support for the purification of crude terephthalic acid is 0.4 g/cm$^3$.

TABLE I

| | Surface Area Changes Upon Plating With Palladium | | |
|---|---|---|---|
| | Surface Area (m$^2$/g) | | Weight percent of |
| Porous Support | Support | Pd-Plated Support | Palladium |
| Titanium | 0.06 | 0.22 | 0.1–2.5 |
| Inconel | 0.03 | 0.55 | 0.1–1.0 |
| Nickel | 0.025 | 1.21 | 0.1–10.0 |

The ability of the low surface area porous metal catalyst to compete with high surface area granular carbon supports is believed due to the accessibility of substantially all of the metal support surface for reaction. Most of the carbon surface area is either too deep in the carbon particle or inaccessible in very small pores to either catalyst metal or reaction medium. Generally only 1% or less of the surface area of 4×8 mesh carbon granulates is catalytically useful. Hence, porous metal catalysts combine the good mass transfer properties of powdered catalysts with the ease of separation from reactions characteristic of monolithic catalysts.

It is also true that porous metal catalysts have relatively uniform pore dimensions, whereas granular catalysts exhibit large void spaces where no reaction can be effected. Channeling is also a problem with the granular catalysts. Beds of porous metal catalysts exhibit higher pressure drops and show catalytic activity even at very short residence times.

Since optimum utilization of these novel catalysts will generally require a different process design from that now employed, as, for example, in purification of terephthalic acid for use in polyester processing, one attractive use of such catalysts involves final purification, or recycle, treatment of a chemical stream. Employing terephthalic acid as an example, final conversion of 4-carboxybenzaldehyde in a recycle operation may be effected at a lower temperature with the catalysts of this invention while lessening the likelihood of other and undesirable chemical conversions occurring.

The following examples are illustrative, without limitation, of the catalytic compositions of this invention and their utility in selected processes.

EXAMPLE I

Porous, sintered titanium support metal was obtained from Imperial Clevite Company, as grade Ti-2505, having a mean pore diameter of 5 microns. The support metal was obtained as 1/16" plate and subsequently cut into desired sizes.

The porous titanium was activated using a two-step procedure. Cleaning was done in a scale-loosening bath using a solution of 5% sodium carbonate and 5% potassium permanganate at 85° C. under stirring for 30 minutes. It was then rinsed with water and the scale removed in a bath containing 15% nitric acid and 2.4% hydrofluoric acid. The titanium was exposed to this bath for three minutes and rinsed with water.

The direct electrolytic deposition of 0.1–2.5 weight percent of palladium (calculated as elemental palladium and based on the weight of the final catalyst composition) onto titanium was done using a dilute solution of palladium chloride in water (0.33 wt.%) in the presence of a large excess of ammonium chloride. It was done at room temperature using palladium as an anode at a current density of 10 amp./ft.$^2$.

EXAMPLE II

To improve adherence of palladium to the porous titanium support a third metal was deposited at a level of 1-10 weight percent of the third metal (calculated as the elemental third metal and based on the weight of the final catalyst composition) as an intermediate layer followed by plating with palladium at a level of 1-4 weight percent of the palladium (calculated as elemental palladium and based on the weight of the final catalyst composition). Three metals were evaluated as intermediate layers: copper, nickel and platinum. They were deposited from solutions of copper sulfate, nickel sulfate and chloroplatinic acid, respectively. The electroplating of these metals onto titanium and the subsequent final electroplating with palladium onto these intermediate metals was done at conditions described in Table II. The same conditions and procedures were used in the final plating with palladium regardless of the intermediate layer. In Table II, the concentration of the first metal is reported as weight percent of the metal calculated as the elemental metal and based on the weight of the catalyst composition.

TABLE II

| Conditions Employed | Plating Conditions Product | | | |
|---|---|---|---|---|
| | Cu/Ti | Ni/Ti | Pt/Ti | Pd/X/Ti[a] |
| Wt. % first metal | 0.1-10 | 0.1-10 | 0.1-4 | 0.1-4 |
| Plating component | $CuSO_4$ | $NiSO_4$ | $H_2PtCl_6$ | $PdCl_2$ |
| Current density, amp./ft.$^2$ | None | 75 | 15 | 15 |
| Anode | None | Ni | Pt | Pd |
| Time, hrs. | 1 | 0.5 | 0.5 | 0.5 |
| Temperature, °C. | Room Temp. | 40 | 90 | 90 |

[a]The same palladium plating procedure was used with either Cu, Ni, or Pt as intermediate layer and with the intermediate metal at 1-10 weight percent, calculated as the elemental intermediate metal and based on the weight of the final catalyst composition.

EXAMPLE III

Porous nickel was obtained from a non-commercial source. Cleaning of the nickel surface was done in a 20% solution of sulfuric acid for ten minutes at room temperature. After rinsing, it was activated in a bath containing 10% nitric acid and 1.5% hydrofluoric acid and rinsed with water. Plating was done according to the conditions and concentration levels described in Example I using nickel instead of titanium as the support metal.

EXAMPLE IV

Batch reactor screening tests were conducted at room temperature and a hydrogen partial pressure of 60 psig in a 250 ml Parr vessel. The vessel was charged with 100 ml of saturated solution of 4-carboxybenzaldehyde in water containing about 450 ppm 4-carboxybenzaldehyde. Catalyst (1 g) was suspended in this solution by a small basket and the solution stirred by a magnet. After purging with nitrogen, hydrogen was added. One hour after hydrogen addition, a samle of the solution was taken, analyzed by liquid chromatography (LC) and the 4-carboxybenzaldehyde content compared to that of the original sample before catalyst addition.

The room temperature batch "screening test" is suitable to distinguish between good, mediocre and poor catalysts, thereby eliminating the need for testing all catalysts in more elaborate autoclave tests.

The results for catalysts prepared as in Example I, II and III are presented in Table III.

TABLE III

| | Conversion of 4-CARBOXYBENZALDEHYE[a] | |
|---|---|---|
| Catalyst | Screening Test[b] | Autoclave Test[c] |
| Pd/C (reference) | 100 | 99 |
| Pd/Ni | 100 | — |
| Pd/Ti | 87 | — |
| Pd/Ni/Ti | 58 | 50 |
| Pd/Cu/Ti | 52 | 64 |
| Pd/Pt/Ti | 43 | 58 |
| Porous Ti | 0 | 0 |

[a]% after 1 hr.
[b]Conditions of Example IV
[c]Conditions of Example V

EXAMPLE V

The catalysts employed in Example IV were tested in a batch reactor at 530° F. A 20% slurry of crude terephthalic acid in water was heated to 530° F. in a one-gallon titanium autoclave. Hydrogen was then charged at a partial pressure of 200 psig. Just before addition of the catalyst a zero time sample as taken and additional samples were taken thereafter for analysis. Test results are presented in Table III.

EXAMPLE VI

Flow reactor tests were conducted at room temperature in equipment consisting of a minireactor which was connected to a feed tank on one side and a receiver on the other side. The system would be evacuated or pressurized with either nitrogen or hydrogen. Liquid flow was regulated by a needle valve. The reactor consisted of an in-line filter holder with an inside diameter of 25.4 mm. It was fitted with four disks of the sintered metal plates to give a length of 6.4 mm. This resulted in a volume of 3.2 ml. During the test a saturated solution of 4-carboxybenzaldehyde in water, with a hydrogen partial pressure of 60 psig, was pushed through the catalyst bed at conditions similar to those employed in Example IV, except that the same solution was recycled through the bed three times and analyzed after each cycle.

When employing a Pd/Ti catalyst, conversion of 4-carboxybenzaldehyde increased after each pass from 36% to 74% and finally to 92%.

EXAMPLE VII

Flow reactor tests were conducted at 530° F. in equipment consisting of a one-gallon titanium autoclave used as feed vessel, to heat up the crude terephthalic acid slurry, and a sampling system used as receiver. By taking samples, the crude terephthalic acid solution was forced to pass through the catalyst. Two disks of catalyst 1/16" in thickness each (total length 3.2 mm) and with a ½" diameter (12.7 mm) were fitted into the reactor sampling line on the bottom of the reactor. An unplated disk separated the palladium-plated disks from the crude terephthalic acid solution in water thereby preventing 4-carboxybenzaldehyde reduction during heat-up.

The concentration of crude terephthalic acid in water was 5%, the hydrogen partial pressure was 200 psig, and the temperature was 530° F. These conditions were similar to the batch reactor test except that a lower crude terephthalic acid concentration was chosen to reduce the change of plugging. The amount of solution which passed through the catalyst each time was about 40 ml, the size of the sample bomb. There was no recycle in this test. By comparing the sample size to the void volume of the catalyst and by estimating the time it took to fill the sample bomb, the residence time in the catalyst bed was calculated. The 4-carboxybenzaldehyde conversion was determined by comparison of its content in samples taken before and after the introduction of hydrogen.

With the Pd/Ti catalyst, conversions of 4-carboxybenzaldehyde ranged from 29.7% to 39.9% at a calculated residence time of only 0.01 sec.

In other evaluation procedures, a porous nickel-based catalyst was tested in a process requiring hydrogenation at or near room temperature in an alkaline medium. The hydrogenation step was part of a process to make p-hydroxymethyl benzoic acid by electrolytic reduction of crude terephthalic acid. Although most of the crude terephthalic acid in this process is reduced to p-hydroxymethyl benzoic acid, it is contaminated by a small amount of 4-carboxybenzaldehyde. A typical product of the electrolytic crude terephthalic acid reduction would contain 13.6% p-hydroxymethyl benzoic acid and 0.33% 4-carboxybenzaldehyde in an ammonia solution. Using a porous nickel-based catalyst electroplated with nickel, the 4-carboxybenzaldehyde was quantitatively converted to p-hydroxymethyl benzoic acid by hydrogen in a short time at room temperature. The above catalyst performed similarly to commercial nickel on silica catalyst, even though it was tested in a batch reactor system.

It was most unexpected that the reduction of 4-carboxybenzaldehyde to p-hydroxymethyl benzoic could be so easily done at the high pH of an ammonia solution since little reduction with this porous nickel catalyst was observed under mildly acid conditions at pH 3.0 temperatures. The reverse has been observed with Pd/C catalyst. Using the above solution from the electrolytic crude terephthalic acid reduction, a blank run was made with porous nickel support only without electroplating. The 4-carboxybenzaldehyde content was reduced from 0.33% to 0.26%, indicating a slight activity of the support.

Results with the Ni/Ni catalyst indicate a wide range of applications for such porous, sintered metal bases with metallic catalyst surface layers.

From the above description, it is apparent that the objects of this invention have been achieved. While only certain embodiments have been set forth, alternative embodiments and various modifications will be apparent from the above description to those skilled in the art. These alternatives are considered to be equivalents and within the spirit and scope of the present invention.

Having described the invention, what is claimed is:

1. A catalyst composition consisting essentially of a first catalytic metal selected from the class consisting of palladium and rhodium and extended as a thin surface layer upon a second support metal selected from the class consisting of titanium, nickel and alloys comprising one or more of said support metals, and afforded as a porous, sintered substrate, wherein the first metal is present at a level of 0.1-10 weight percent, calculated as the elemental first metal and based on the weight of the catalyst composition.

2. The catalyst composition of claim 1 wherein the first catalytic metal is palladium.

3. The catalyst composition of claim 1 wherein the second support metal is titanium.

4. The catalyst composition of claim 1 wherein an intermediate metal layer selected from the class consisting of copper, platinum and mixtures thereof is first extended upon the surface of the second support metal, wherein the intermediate metal is present at a level of 0.1-10 weight percent, calculated as the elemental intermediate metal and based on the weight of the catalyst composition.

5. The catalyst composition of claim 1 wherein the surface area is within the range from about 0.01 to about 10 square meters per gram.

6. The catalyst composition of claim 1 wherein the pore diameter is within the range from about 1 to about 10 microns.

7. The catalyst composition of claim 1 wherein the first catalytic metal is palladium and the second support metal is titanium.

8. An improved hydrogenation catalyst composition consisting essentially of a first catalytic hydrogenation metal selected from the class consisting of palladium and rodium and extended as a thin surface layer upon a second support metal, selected from the class consisting of titanium, nickel and alloys comprising one or more of said support metals, and said support metal being present as a porous, sintered substrate, wherein the first metal is present at a level of 0.1-10 weight percent, calculated as the elemental first metal and based on the weight of the catalyst composition.

9. The catalyst composition of claim 8 wherein the first catalytic metal is palladium.

10. The catalyst composition of claim 8 wherein the second support metal is titanium.

11. The hydrogenation catalyst composition of claim 8 wherein an intermediate metal layer selected from the class consisting of copper, platinum and mixtures thereof is first extended upon the surface of the second support metal, wherein the intermediate metal is present at a level of 0.1-10 weight percent, calculated as the elemental intermediate metal and based on the weight of the catalyst composition.

12. The catalyst composition of claim 8 wherein the first catalytic metal is palladium and the second support metal is titanium.

13. An improved decarbonylation catalyst composition consisting essentially of a first catalytic decarbonylation metal selected from the class consisting of palladium and rhodium, and extended as a thin surface layer upon a second support metal selected from the class consisting of titanium, nickel and alloys comprising one or more of said support metals, said support metal being provided as a porous, sintered substrate and being present at a level of 0.1-10 weight percent, calculated as the elemental first metal and based on the weight of the catalyst composition.

14. The decarbonylation catalyst composition of claim 13 wherein an intermediate metal layer is first extended upon the surface of the second support metal, said intermediate metal being selected from the class consisting of copper, nickel, platinum and mixtures thereof and being present at a level of 0.1-10 weight percent, calculated as the elemental intermediate metal and based on the weight of the catalyst composition.

15. The decarbonylation catalyst composition of claim 13 wherein the first catalytic metal is palladium and the second support metal is titanium.

16. A monolithic metal catalyst composition for use in the purification of terephthalic acid by conversion of 4-carboxybenzaldehyde contaminant, consisting essentially of a porous, sintered metallic support selected from the class consisting of titanium, nickel and alloys thereof, and having dispersed on the surface thereof a layer of catalyst metal, said catalyst metal being selected from the class consisting of palladium, rhodium, and mixtures thereof and being present at a level of 0.1–10 weight percent, calculated as the elemental catalytic metal and based on the weight of the catalyst conposition.

17. The monolithic metal catalyst composition of claim 16 wherein the catalyst metal is palladium and the porous, sintered metallic support is titanium.

* * * * *